(12) United States Patent
Luu et al.

(10) Patent No.: US 7,166,642 B1
(45) Date of Patent: *Jan. 23, 2007

(54) USE OF CYCLOHEXENONE LONG-CHAIN ALCOHOL FOR TREATING NEURODEGENERATIVE DISEASES

(75) Inventors: Bang Luu, Strasbourg (FR); Gaby Schmitt, Strasbourg (FR); Florence Keyling-Bilger, Strasbourg (FR); Celine Girlanda-Junges, Strasbourg (FR); Jean-Philippe Loeffler, Strasbourg (FR); Bernadette Lutz-Bucher, Strasbourg (FR); Jose-Luis Gonzalez de Aguilar, Strasbourg (FR); Masashi Yamada, Tokyo (JP); Yukie Suma, Tokyo (JP); Philippe Chabert, Strasbourg (FR)

(73) Assignee: Meiji Dairies Corporation, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/890,969

(22) PCT Filed: Feb. 10, 2000
(Under 37 CFR 1.47)

(86) PCT No.: PCT/JP00/00742
§ 371 (c)(1),
(2), (4) Date: Apr. 11, 2002

(87) PCT Pub. No.: WO00/47199
PCT Pub. Date: Aug. 17, 2000

(30) Foreign Application Priority Data

Feb. 10, 1999 (JP) .................................. 11/033312
Jun. 25, 1999 (JP) .................................. 11/180546

(51) Int. Cl.
*A61K 31/12* (2006.01)
*A61K 31/045* (2006.01)

(52) U.S. Cl. ....................................... 514/690; 514/729
(58) Field of Classification Search ................ 514/730, 514/688, 689, 690, 729
See application file for complete search history.

(56) References Cited

U.S. PATENT DOCUMENTS 5,447,959 A * 9/1995 Borg .......................... 514/725

(Continued)

FOREIGN PATENT DOCUMENTS

EP          0 593 831          4/1994

(Continued)

OTHER PUBLICATIONS

Girlanda-Junges et al, 129CA:144553, 1998.*

(Continued)

*Primary Examiner*—Shengjun Wang
(74) *Attorney, Agent, or Firm*—Oblon, Spivak, McClelland, Maier & Neustadt, P.C.

(57) ABSTRACT

A preventive and therapeutic drug for a neurodegenerative disease containing, as an active ingredient, a cyclohexenone long-chain alcohol compound represented by formula (1) wherein each of $R^1$, $R^2$, and $R^3$ represents a hydrogen atom or a methyl group; and X represents a C10–C28 alkylene group or alkenylene group. Since the compound of the present invention exhibits excellent neurite-extension ability and an inhibition effect on disorders caused by mutation in an SOD gene, it is useful as the active ingredient of a preventive and therapeutic drug for neurodegenerative diseases, inter alia, amyotrophic lateral sclerosis, and as the active ingredient of an inhibitory drug for disorders caused by mutation in an SOD gene.

10 Claims, 1 Drawing Sheet

U.S. PATENT DOCUMENTS 5,731,354 A * 3/1998 Pruss .................. 514/723
6,228,893 B1    5/2001 Luu et al.

FOREIGN PATENT DOCUMENTS

| WO | WO 91/05754 | 5/1991 |
| WO | WO 94/19493 | 9/1994 |
| WO | WO 96/21438 | 7/1996 |
| WO | WO 99/08987 | 2/1999 |

OTHER PUBLICATIONS

Girlanda-Junges et al, Tetrahedron, vol. 54, pp. 7735-7748, 1998.*

Girlanda-Junges et al. "Effect of Cyclohexenoic Long Chain Fatty Alcohols on Neurite Outgrowth" 1998, Tetrahedron, 54, 7735-7748.*

Rosen et al. "Mutations in Cu/Zn superoxide dismutase gene are associated with familiar amyotrophic lateral sclerosis" 1993, Nature, 362, 59-62.*

Céline Girlanda-Junges, et al., Tetrahadron, vol. 54, No. 27, pp. 7735-7748, "Effect of Cyclohexenonic Long Chain Fatty Alcohols on Neurite Outgrowth, Study on Structure-Activity Relationship", Jul. 2, 1998.

V. Doppler, et al., Clinical Pharmacology, vol. 18, p. 205, "Short Term Safety Controlled Trial of SR 57746A in Amyotrophic Lateral Sclerosis", Sep. 18, 1996.

U.S. Appl. No. 10/550,305, filed Sep. 22, 2005, Luu et al.

U.S. Appl. No. 09/890,969, filed Apr. 11, 2002, Luu et al.

* cited by examiner

USE OF CYCLOHEXENONE LONG-CHAIN ALCOHOL FOR TREATING NEURODEGENERATIVE DISEASES

TECHNICAL FIELD

The present invention relates to a preventive and therapeutic drug for neurodegenerative diseases.

BACKGROUND ART

Typical neurodegenerative diseases include Alzheimer's disease and Pick's disease, which mainly affect the cerebral cortex; Parkinson's disease and Huntington's chorea, which mainly affect the basal ganglia; spinal cord-cerebellum degenerative disease, which mainly affects the cerebellum; and amyotrophic lateral sclerosis, which mainly affects the spinal cord. Neurodegenerative disease is rarely defined, even in textbooks. A possible definition for neurodegenerative disease may be as follows: a progressive disease which involves disorders of a certain system (such as the pyramidal tract system, funiculus dorsalis system, or spinal cord-cerebellum system) alone or in combination so as to manifest clinical symptoms which progress slowly and gradually, and for which the real cause cannot be determined (Ichiro KANAZAWA: Sai-shin Naikagaku Taikei, 68: p. 3, Nakayama Shoten (1997)).

Amyotrophic lateral sclerosis (ALS) is a lethal neurodegenerative disease characterized by a selective disorder of motor neurons in the cerebral cortex, brain stem, and spinal cord, and the primary symptoms of ALS include progressive amyotrophia and hyper-reflex of deep tendon. Recently, there have been reported several cases, one after another, of spot mutations of Cu/Zn superoxide dismutase (SOD), which is a causal gene with respect to familial amyotrophic lateral sclerosis (FALS) and sporadic amyotrophic lateral sclerosis (SALS), and these reports have received much attention (Deng, H. et al.: *Science*, 261: 1047–1051, 1993; Rosen DR. et al.: *Nature*, 363: 59–62, 1993: Jones, CT. et al.: *Lancet*, 342: 1050–1061, 1993).

In efforts toward curing ALS, neuroprotective agents (anti-oxidants or anti-stimulants), neuroregeneratives and neurotrophic factors have been used, but only very weak effects have been observed. Specifically, the actions of ciliary neurotrophic factor (CNTF), insulin growth factor-1 (IGF-1), brain-derived neurotrophic factor (BDNF) and nerve growth factor (NGF) against motor neuron injury have been reported, but the effects of these actions have remained weak and unsatisfying.

DISCLOSURE OF THE INVENTION

In view of the foregoing, an object of the present invention is to provide a novel preventive and therapeutic drug for neurodegenerative diseases, including ALS.

The present inventors have already applied for a patent (PCT/JP98/03560), based on the finding that a long-chain alcohol having a cyclohexenone skeleton exhibits excellent neurite-extension ability and the possible usefulness as a nerve growth factor. Thereafter, the present inventors have found that administration of the alcohol compound to transgenic mice having missense mutation in a Cu/Zn SOD-1 gene prolongs the mice's life span significantly as compared with those of the control group, and hence that the compound is useful as a preventive and therapeutic drug for the neurodegenerative diseases, inter alia, ALS, due to degeneration of a motor neuron attributed to expression of an SOD-1 mutant gene. The present invention has been accomplished based on this finding.

Accordingly, the present invention provides a preventive and therapeutic drug for a neurodegenerative disease containing, as an active ingredient, a cyclohexenone long-chain alcohol compound represented by the following formula (1):

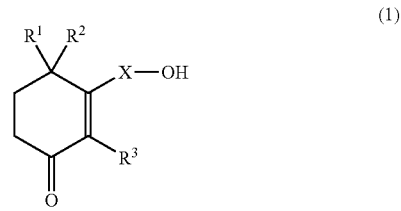

wherein each of $R^1$, $R^2$, and $R^3$ represents a hydrogen atom or a methyl group; and X represents a C10–C28 linear or branched alkylene group or alkenylene group.

Further, the present invention provides use of the cyclohexenone long-chain alcohol compound represented by the formula (1) for the production of a preventive and therapeutic drug for a neurodegenerative disease.

Still, the present invention provides a method for treating a neurodegenerative disease, which method comprises administering the cyclohexenone long-chain alcohol compound represented by formula (1) to a patient in need thereof.

BEST MODES FOR CARRYING OUT THE INVENTION

Figure 1:
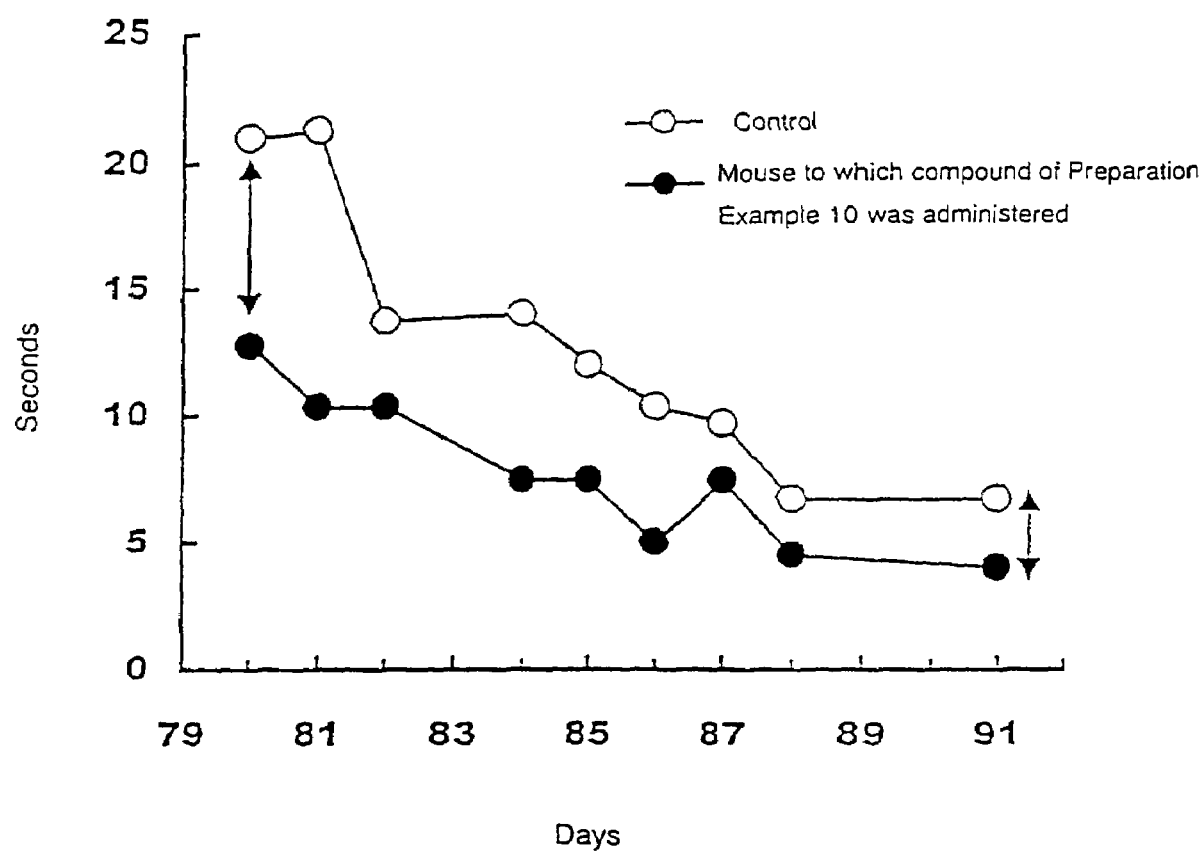
FIG. 1 shows the results of bar test in transgenic mice expressing the mutant SOD-1 gene.

In the above compound of formula (1), the examples of the side chains of the branched alkylene or alkenylene group of X include a C1–C10 alkyl group. Examples of the alkyl side chain groups include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group, an isohexyl group, a heptyl group, an octyl group, a nonyl group, and a decyl group. Of these, a decyl group is particularly preferred. The linear alkylene group or alkenylene group, which refers to an alkene structure having at least one carbon—carbon double bond, is preferably substituted at different positions of the side chain. Of these Xs, a linear C10–C28 alkylene group is preferred, with a linear C10–C18 alkylene group being more preferred. Meanwhile, as to $R^1$, $R^2$, and $R^3$, each of which represents a hydrogen atom or a methyl group, it is preferred when at least one of the three is a methyl group.

The compound of formula (1) may assume the form of a pharmaceutically acceptable salt thereof, or a solvate or hydrate thereof. The compound of formula (1) has a variety of possible isomers, which are also encompassed by the present invention.

The compound of formula (1) of the present invention can be prepared, for example, in accordance with the following reaction process A or B.

[Process A]

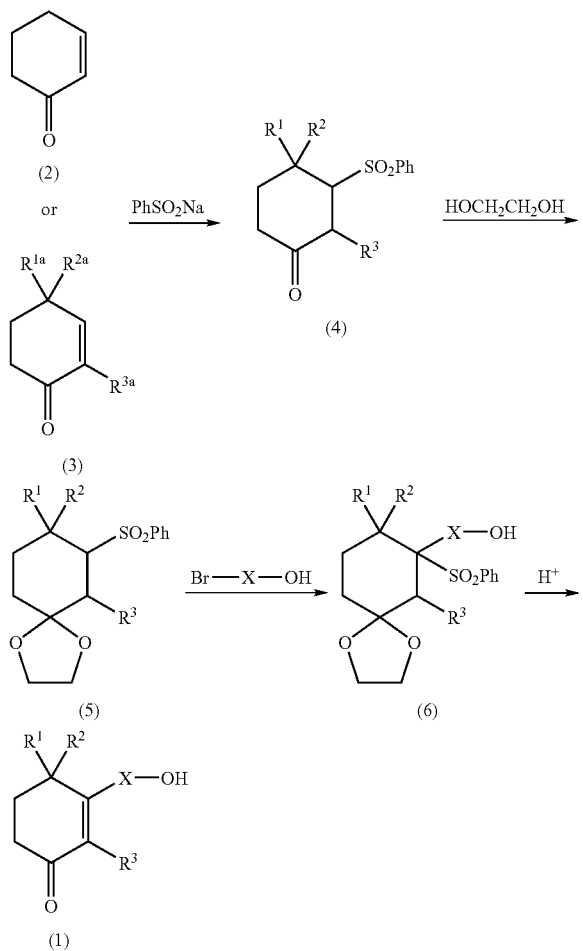

wherein $R^{1a}$, $R^{2a}$ and $R^{3a}$ each independently represents a hydrogen atom or a methyl group, with the proviso that at least one of them represents a methyl group, Ph represents a phenyl group and R1, R2 and R3 have the same meaning as defined above.

Specifically, the invention compound of formula 1 (1) can be obtained by reacting cyclohexenone (2) or methyl-substituted-2-cyclohexene-1-one (3) with a benzenesulfinic acid salt in the presence of an acid to obtain compound (4), reacting the resulting compound (4) with ethylene glycol to obtain its ketal derivative (5), reacting the resulting derivative (5) with a ω-halogenoalkanol or ω-halo genoalkenol to obtain compound (6), followed by subjecting compound (6) to an acid treatment to eliminate the protective group.

The methyl-substituted-2-cyclohexen-1-one (3) used here as a raw material is available by reacting methyl-substituted cyclohexanone with a trialkylsilyl halide in the presence of butyl lithium, followed by oxidation in the presence of a palladium catalyst.

In the above reaction, the reaction between cyclohexanone (2) or methyl-substituted-2-cyclohexen-1-one (3) and a benzenesulfinic acid salt, for example, benzenesulfinic acid sodium is preferably effected in the presence of an acid such as hydrochloric acid, sulfuric acid or phosphoric acid at 0 to 100° C. for 5 to 40 hours.

The reaction between compound (4) and ethylene glycol is preferably carried out in the presence of a condensing agent such as paratoluenesulfonic anhydride at 50 to 120° C. for 1 to 10 hours.

As a ω-halogenoalkanol to be reacted with the ketal derivative (5), a ω-bromoalkanol is preferred. It is desirable that the reaction between the ketal derivative (5) and a ω-bromoalkanol be carried out in the presence of a metal compound such as butyl lithium under low-temperature conditions.

The elimination of the phenylsulfonyl and ketal-protective groups from compound (6) is preferably effected by reacting compound (6) with an acid such as paratoluenesulfonic acid.

[Process B]

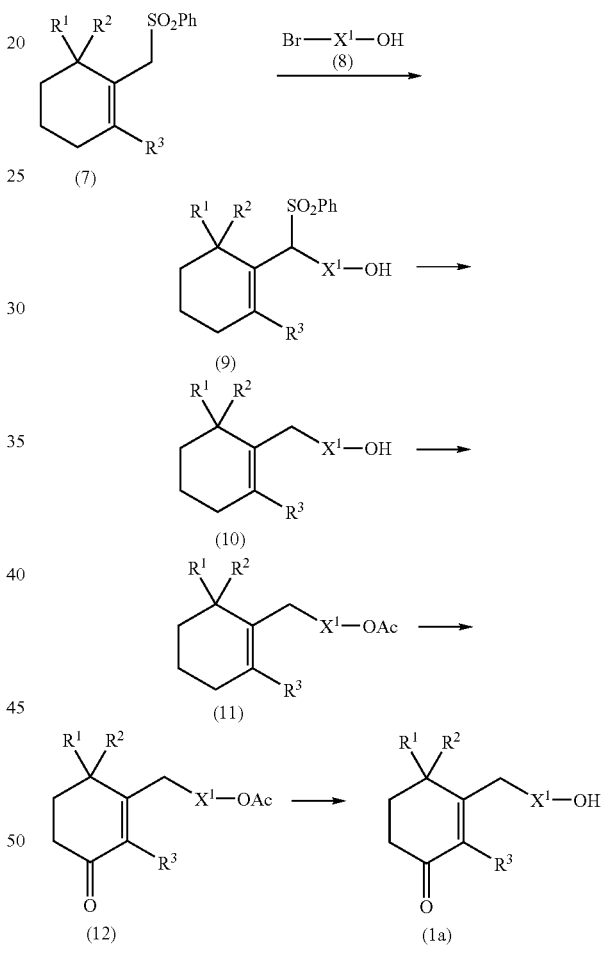

wherein X1 represents $C_{9-27}$ alkylene group or $C_{9-27}$ alkenylene group, Ac represents an acyl group, $R^1$, $R^2$, $R^3$ and Ph have the same meaning as defined above.

Specifically, compound (7) (obtained, for instance, through the method described in *Tetrahedron*, 1996, vol. 52, 14891–14904) is reacted with ω-bromoalcohol to obtain compound (9), subsequently the phenylsulphonyl group of the resulting compound being eliminated to give compound (10), followed by protection of the hydroxy group of compound (10) to yield compound (11). The resulting compound is subsequently oxidized to obtain compound (12), and the hydroxy-protective group of the resulting compound is then eliminated to obtain compound (12).

The reaction between compound (7) and compound (8) is preferably carried out at low temperatures in the presence of a metal compound such as butyl lithium.

The elimination of the phenylsulphonyl group from compound (9) may be conducted by reacting the compound and a phosphate in the presence of sodium amalgam.

As a hydroxy-protective group of compound (10), the acetyl group is preferred, the protection reaction being preferably performed, for example, by reacting compound (10) and acetic anhydride.

The oxidation reaction of compound (11) may preferably be performed by reacting the compound and alkyl hydroperoxide such as t-butyl hydroperoxide in the presence of a metal compound such as ruthenium trichloride.

The elimination reaction of the protective group of compound (12) is preferably performed by hydrolyzing the compound in the presence of a base such as potassium carbonate.

As described hereinabove, since mutation in a Cu/Zn SOD (SOD-1) gene is found in a portion of cases of FALS and SALS, the effect of administration of compound (1) to transgenic mice on prolongation of survival time has been investigated. The transgenic mice employed are those in which Gly-86 in the fourth exon of a mouse SOD-1 gene is mutated to Arg (G86R) (Ripps M. E., et al.: *Proc. Natl. Acad. Sci. USA*. 92: 689–693, 1995). Another expression of the mutant gene in the central nervous system of transgenic mice produces rapidly progressive and aging-related deterioration of motor functions concomitant with degeneration of motor neurons of the spinal cord, brain stem, and neocortex (Ripps M. E., et al.: *Proc. Natl. Acad. Sci. USA*. 92: 689–693, 1995). Administration of compound (1) to the transgenic mice prolongs significantly their lives as compared with those of the control group.

At present, the mechanism of remarkable prolongation of the survival time of transgenic mice by administration of compound of formula (1) is unknown. Results of experiments conducted in the present invention indicate that the compound of formula (1) is useful for preventing and curing disorders caused by expression of a SOD mutant gene. As shown in Table 1, compound (1) exhibits excellent.

As shown in Table 1, the compound of formula (1) exhibits excellent neurite-extension effect on neurons originating from the cerebral hemisphere of rat fetus. In particular, Compound Nos. 9, 10, 20, 23, and 24 exhibit remarkably excellent neurite-extension effect as compared with bFGF.

Briefly, the compound of formula (1) has an inhibitory effect on disorders caused by mutation in an SOD gene and exhibits a neurotrophic factor effect such as acceleration of neurite-extension by acting directly on neurons. Thus, the compound of formula (1) is useful for preventing and curing disorders caused by mutation in an SOD gene or neurodegenerative diseases.

The compound of formula (1) may be administered through either an oral route or a parenteral route, such as intramuscular injection, subcutaneous injection, intravenous injection, or administration by use of a suppository.

A formulation for oral administration is prepared by adding excipients and optional additives such as binders, disintegrators, lubricants, colorants, and flavoring agents and by forming into tablets, coated-tablets, granules, capsules, solutions, syrups, elixirs, oily or aqueous suspensions, etc. through a customary method. Examples of excipients include lactose, corn starch, saccharose, glucose, sorbitol, and crystalline cellulose. Examples of binders include polyvinyl alcohol, polyvinyl ether, ethylcellulose, methylcellulose, acacia, tragacanth, gelatin, shellac, hydroxypropyl cellulose, hydroxypropyl starch, and polyvinyl pyrrolidone.

Examples of disintegrators include starch, agar, gelatin powder, crystalline cellulose, calcium carbonate, sodium hydrogencarbonate, calcium citrate, dextran, and pectin. Examples of lubricants include magnesium stearate, talc, polyethylene glycol, silica, and hardened vegetable oil. Colorants are those allowed to be incorporated into pharmaceuticals. Examples of the flavoring agents which may be used include cocoa powder, menthol, aromatic acid, peppermint oil, borneol, and cinnamon powder. The tablets and granules may be coated with sugar, gelatin, and other coatings according to needs.

An injection preparation is prepared by adding optional pH-regulators, buffers, stabilizers, preservatives, etc. and by forming into a formulation for subcutaneous injection, intramuscular injection, or intravenous injection. The injection preparation may have a solid form through introduction into a container and subsequent treatment such as lyophilization for dissolution upon use. The injection formulation may be charged into a container for a single dose or a plurality of divided doses.

When the compound of the present invention is administered as a drug, the daily dose for a human adult is typically 0.01–1000 mg, preferably 0.1–100 mg. The compound may be administered at a single time or in a divided manner (2–4 times).

EXAMPLES

The present invention will next be described in detail by way of examples, which should not be construed as limiting the invention thereto.

Preparation Example 1

(1) Benzenesulfinic acid sodium salt (10.25 g) was added to a solution containing 5 ml of cyclohexenone and 30 ml of water, followed by the dropwise addition of 60 ml of 1N hydrochloric acid. The reaction mixture was stirred at room temperature for 24 hours. The crystals so precipitated were filtered and then washed with water, isopropanol and cold ethyl ether. After recrystallization from isopropanol, 5.74 g of 3-(phenylsulfonyl)-cyclohexan-1-one (m.p.: 83–85° C.) were obtained in the form of white crystals. Yield: 97%

(2) To a solution of 5.3 g of 3-(phenylsulfonyl)-cyclohexan-1-one in 60 ml of benzene, were added 0.3 ml of 1,2-ethanediol and 0.2 g of anhydrous paratoluenesulfonic acid. The reaction mixture was heated under reflux for 4 hours. After the reaction, a 2M aqueous sodium bicarbonate solution was added and the resulting mixture was extracted with ethyl acetate three times. The combined organic layers were washed with saturated saline and then, dried over magnesium sulfate. The solvent was distilled off under reduced pressure. The residue was recrystallized from ethyl ether, whereby 6.1 g of 1,1-(ethylenedioxy)-3-(phenylsulfonyl)-cyclohexane (m.p.: 93–95° C.) were obtained in the form of white crystals. Yield: 97%

(3) A solution of n-butyl lithium (2 ml) was added dropwise to a solution of 565 mg of 1,1-(ethylenedioxy)-3-(phenylsulfonyl)-cyclohexane and 4 mg of triphenylmethane in 5 ml of THF at −78° C. under an argon gas stream. After stirring for 10 minutes, the reaction was effected at room temperature for 1 hour. HMPT (1 ml) was added. The solution was stirred at room temperature for 1 hour after recooling to −78. A solution of 159 mg of 10-bromo-1-decanol in 2 ml of THF was added dropwise to the reaction mixture.

After reaction at −20° C. for 2 hours, the reaction mixture was poured into a saturated solution of ammonium chloride. The resulting mixture was extracted with ethyl ether. The organic layer was washed with water and saturated saline and then, dried over anhydrous magnesium sulfate. The solvent was distilled off under reduced pressure. The residue was purified by chromatography on a silica gel column while using hexane-ethyl acetate, whereby 265 mg of 1,1-(ethylenedioxy)-3-(10-hydroxydecyl)-3-(phenylsulfonyl)-cyclohexane were obtained in the form of a colorless oil. Yield: 90%

(4) Paratoluenesulfonic acid (20 mg) was added to a solution of 193 mg of 1,1-(ethylenedioxy)-3-(10-hydroxydecyl)-3-(phenylsulfonyl)-cyclohexane in 3 ml of chloroform and 0.6 ml of acetone. To the resulting mixture was added 10 ml of a saturated aqueous solution of sodium bicarbonate, followed by extraction with dichloromethane. The organic layer was washed with saturated saline and dried over magnesium sulfate. The solvent was distilled off under reduced pressure. The residue was purified by chromatography on a silica gel column using hexane-ethyl acetate, whereby 86 mg of 3-(10-hydroxydecyl)-2-cyclohexen-1-one were obtained in the form of a colorless oil. Yield: 77%

In a similar manner to Preparation Example 1, the following compounds were obtained.

Preparation Example 2

3-(1-hydroxy-undecyl)-2-cyclohexen-1-one (Melting Point: 34 to 35° C.).

Preparation Example 3

3-(12-hydroxy-dodecyl)-2-cyclohexen-1-one (Melting Point: 35 to 36° C.).

Preparation Example 4

3-(β-hydroxy-tridecyl)-2-cyclohexen-1-one (Melting Point: 42 to 43° C.).

Preparation Example 5

3-(14-hydroxy-tetradecyl)-2-cyclohexen-1-one (Melting Point: 44 to 45° C.).

Preparation Example 6

(1) A 1.4M n-butyllithium solution (35.4 ml) was added dropwise to a solution of 7 ml of N,N-diisopropylamine in 20 ml of THF at −78° C. The resulting mixture was stirred at 0° C. for 30 min. Four ml of 4-methylcyclohexan-1-one in 10 ml of THF at −78° C. was added dropwise to the LDA solution. After stirring at −78° C. for 1 hour, 6.5 ml of trimethylsilyl chloride were added to the reaction mixture. The resulting mixture was stirred at room temperature for 1 hour and then poured into an aqueous solution of sodium bicarbonate, followed by extraction with ethyl ether. The organic layer was washed with saturated saline and dried over magnesium sulfate. The solvent was distilled off under reduced pressure. The residue was purified by distillation under reduced pressure, whereby 5.83 g of 4-methyl-1-(trimethylsilyloxy)-1-cyclohexene were obtained. Yield: 96% TLC:(hexane-AcOET:8-2)Rf=0.8

(2) A catalyst amount of palladium (II) acetate was added to a solution of 3.53 g of 4-methyl-1-(trimethylsilyloxy)-1-cyclohexene in 70 ml of DMSO, followed by stirring while introducing oxygen for 6 hours. After the addition of water at 0° C., the reaction mixture was filtered over celite and then extracted with ethyl ether. The solvent was distilled off under reduced pressure and the residue was dissolved in hexane-water. The resulting solution was extracted with hexane. The hexane layer was washed with saturated saline and dried over magnesium sulfate. The solvent was distilled off under reduced pressure, whereby 4-methyl-2-cyclohexen-1-one was obtained in the form of an oil. Yield: 72% TLC:(hexane-AcOET:8-2)Rf=0.35

(3) Benzenesulfinic acid sodium salt (3.0 g) was added to a solution containing 1.52 g of 4-methyl-2-cyclohexene-1-one and 9 ml of water. 1N Hydrochloric acid (18 ml) was added dropwise to the resulting solution. After stirring at room temperature for 24 hours, the crystals so precipitated were filtered and washed with water, isopropanol and cold ethyl ether. After recrystallization from isopropanol, 4-methyl-3-(phenylsulfonyl)-cyclohexan-1-one (m.p.: 71–74) was obtained in the form of white crystals. Yield: 72%

(4) To a solution of 2.45 g of 4-methyl-3-(phenylsulfonyl)-cyclohexan-1-one in 40 ml of benzene, were added 0.7 ml of 1,2-ethanediol and 0.2 g of anhydrous paratoluenesulfonic acid. The resulting mixture was heated under reflux for 4 hours. After the reaction, a 2M aqueous sodium bicarbonate solution was added and the resulting mixture was extracted with ethyl acetate three times. The combined organic layers were washed with saturated saline, and dried over magnesium sulfate. The solvent was then distilled off under reduced pressure. The residue was recrystallized from ethyl ether, whereby 1,1-(ethylenedioxy)-4-methyl-3-(phenylsulfonyl)-cyclohexane was obtained in the form of white crystals. Yield: 97%, Melting point: 105 to 106° C.

(5) A solution of n-butyl lithium (1.8 ml) was added dropwise to a solution of 560 mg of 1,1-(ethylenedioxy)-4-methyl-3-(phenylsulfonyl)-cyclohexane and 4 mg of triphenylmethane in 5 ml of THF under argon stream at −78° C. The resulting mixture was stirred for 10 minutes and then reacted at room temperature for 1 hour. HMPA (1 ml) was added and the resulting mixture was recooled to −78° C., followed by the dropwise addition of a solution of 166 mg of 10-bromo-1-decanol in 2 ml of THF. After stirring the reaction at −20° C. for 2 hours, the reaction mixture was poured into a saturated solution of ammonium chloride. The resulting mixture was extracted with ethyl ether. The organic layer was washed with water and saturated saline and then, dried over magnesium sulfate. The solvent was distilled off under reduced pressure. The residue was purified by chromatography on a silica gel column while using hexane-ethyl acetate, whereby 1,1-(ethylenedioxy)-3-(10-hydroxydecyl)-4-methyl-3-(phenylsulfonyl)-cyclohexane was obtained in the form of a colorless oil. Yield: 97%, TLC: (hexane-AcOEt: 6-4) Rf=0.14

(6) Paratoluenesulfonic acid (20 ml) was added to a solution of 235 mg of 1,1-(ethylenedioxy)-3-(10-hydroxydecyl)-4-methyl-3-(phenylsulfonyl)-cyclohexane in 20 ml of chloroform and 4 ml of acetone. The resulting mixture was reacted at 50° C. for 24 hours. To the reaction mixture were added 10 ml of a saturated aqueous solution of sodium bicarbonate, followed by extraction with dichloromethane. The organic layer was washed with saturated saline and dried over magnesium sulfate. The solvent was distilled off under reduced pressure. The residue was purified by chromatography on a silica gel column while using hexane-ethyl acetate, whereby 3-(10-hydroxydecyl)-4-methyl-2-cyclohexene-1-one was obtained in the form of a colorless oil. Yield: 75%, CCM: (hexane-AcOEt: 6-4) Rf=0.2

In a similar manner to Preparation Example 6, the following compounds were obtained.

Preparation Example 7

3-(11-hydroxyundecyl)-4-methyl-2-cyclohexen-1-one (TLC: (hexane-AcEt:6-4)Rf=0.21).

Preparation Example 8

3-(12-hydroxydodecyl)-4-methyl-2-cyclohexen-1-one (TLC: (hexane-AcEt:6-4)Rf=0.22).

Preparation Example 9

3-(β-hydroxytridecyl)-4-methyl-2-cyclohexen-1-one (TLC: (hexane-AcEt:6-4)Rf=0.25).

Preparation Example 10

3-(14-hydroxytetradecyl)-4-methyl-2-cyclohexen-1-one (TLC: (hexane-AcEt:6-4)Rf=0.3).

Preparation Example 11

(1) Benzenesulfinic acid sodium salt (5.98 g) was added to a solution containing 3 ml of 4,4-dimethyl-2-cyclohexene-1-one and 20 ml of water. Forty ml of 1N hydrochloric acid were added dropwise to the resulting mixture. The reaction mixture was stirred at room temperature for 24 hours. The crystals so precipitated were filtered and the solid, washed with water, isopropanol and cold ethyl ether. After recrystallization from isopropanol, 4,4-dimethyl-3-(phenylsulfonyl)-cyclohexan-1-one was obtained in the form of white crystals. Yield: 89%, Melting point: 84 to 86° C.

(2) To a solution obtained by dissolving 4.4 g of 4,4-dimethyl-3-(phenylsulfonyl)-cyclohexan-1-one in 45 ml of benzene, were added 1.1 ml of 1,2-ethanediol and 0.3 g of anhydrous paratoluenesulfonic acid. The resulting mixture was heated under reflux for 4 hours. After the reaction, a 2M aqueous sodium bicarbonate solution was added and the resulting mixture was extracted with ethyl acetate three times. The combined organic layers were washed with saturatd saline and dried over magnesium sulfate. The solvent was distilled off under reduced pressure, followed by recrystallization from ethyl ether, whereby 4,4-dimethyl-1,1 (ethylenedioxy)-3-(phenylsulfonyl)-cyclohexane was obtained in the form of white crystals. Yield: 84%, Melting point: 113 to 115° C.

(3) A solution n-butyl lithium (2.93 ml) was added dropwise to a solution of 930 mg of 4,4-dimethyl-1,1-(ethylenedioxy)-3-(phenylsulfonyl)-cyclohexane and 4 mg of triphenylmethane in 5 ml of THF at −78° C. under an argon stream. After stirring for 10 minutes, the mixture was reacted at room temperature for one hour. HMPA (1 ml) was added to the reaction mixture, followed by recooling to −78° C. A solution of 236 mg of 10-bromo-1-decanol in 2 ml of THF was added dropwise to the reaction mixture.

After the reaction at −20° C. for 2 hours, the reaction mixture was poured into a saturated solution of ammonium chloride. The resulting mixture was extracted with ethylether. The organic layer was washed with water and saturated saline, and dried over magnesium sulfate. The solvent was then distilled off under reduced pressure. The residue was purified by chromatography on a silica gel column while using hexane-ethyl acetate, whereby 4,4-dimethyl-1,1-(ethylenedioxy)-3-(10-hydroxydecyl)-3-(phenylsulfonyl)-cyclohexane was obtained in the form of a colorless oil. Yield: 94%, TLC: (hexane-AcOEt: 6-4) Rf=0.15

(4) Paratoluenesulfonic acid (20 mg) was added to a solution of 400 mg of 4,4-dimethyl-1,1-(ethylenedioxy)-3-(10-hydroxydecyl)-3-(phenylsulfonyl)-cyclohexane in 30 ml of chloroform and 6 ml of acetone. The resulting mixture was reacted at 50° C. for 24 hours. To the reaction mixture, were added 10 ml of a saturated sodium bicarbonate solution, followed by extraction with dichloromethane. The organic layer was washed with saturated saline and dried over magnesium sulfate. The solvent was then distilled off under reduced pressure. The residue was purified by chromatography on a silica gel column while using hexane-ethyl acetate, whereby 4,4-dimethyl-3-(10-hydroxydecyl)-2-cyclohexen-1-one was obtained in the form of a colorless oil. Yield: 78%, TLC: (hexane-AcOEt: 6-4) Rf=0.25

In a similar manner to Preparation Example 11, the following compounds were obtained.

Preparation Example 12

3-(11-hydroxyundecyl)-4,4-dimethyl-2-cyclohexen-1-one (TLC: (hexane-AcOEt:6-4)Rf=0.25).

Preparation Example 13

3-(12-hydroxydodecyl)-4,4-dimethyl-2-cyclohexen-1-one (TLC: (hexane-AcOEt:6-4)Rf=0.27).

Preparation Example 14

3-(β-hydroxytridecyl)-4,4-dimethyl-2-cyclohexen-1-one (TLC: (hexane-AcOEt:6-4)Rf=0.3).

Preparation Example 15

3-(14-hydroxytetradecyl)-4,4-dimethyl-2-cyclohexen-1-one (TLC: (hexane-AcOEt:6-4)Rf=0.3).

Preparation Example 16

(1) Benzenesulfinic acid sodium salt (2.9 g) was added to a solution containing 1.5 g of 2-methyl-2-cyclohexen-1-one and 8 ml of water. Then 16 ml of 1N hydrochloric acid was added dropwise to the resulting mixture. The reaction mixture was stirred at room temperature for 24 hours. The crystals so precipitated were filtered and then, washed with water, isopropanol and cold ethyl ether. After recrystallization from isopropanol, 2-methyl-3-(phenylsulfonyl)-cyclohexan-1-one was obtained in the form of white crystals. Yield: 93%, TLC: (hexane-AcOEt: 6-4) Rf=0.25

(2) To a solution obtained by dissolving 1.4 g of 2-methyl-3-(phenylsulfonyl)-cyclohexan-1-one in 20 ml of benzene, were added 0.41 ml of 1,2-ethanediol and 0.1 g of anhydrous paratoluenesulfonic acid. The resulting mixture was heated under reflux for 4 hours. After the reaction, a 2M aqueous sodium bicarbonate solution was added and the resulting mixture was extracted with ethyl acetate three times. The combined organic layers were washed with saturated saline and dried over magnesium sulfate. The solvent was distilled off under reduced pressure. The residue was recrystallized from ethyl ether, whereby 1,1-(ethylenedioxy)-2-methyl-3-

(phenylsulfonyl)-cyclohexane was obtained in the form of white crystals. Yield: 95%, Melting point: 76 to 77° C.

(3) A solution of n-butyl lithium (1.02 ml) was added dropwise to a solution of 304 mg of 1,1-(ethylenedioxy)-2-methyl-3-(phenylsulfonyl)-cyclohexane and 4 mg of triphenylmethane in 5 ml of THF at −78° C. under an argon stream. After stirring for 10 minutes, the reaction was effected at room temperature for 1 hour. HMPA (1 ml) was added to the reaction mixture. It was then recooled to −78° C., followed by the dropwise addition of a solution of 90 mg of 10-bromo-1-decanol in 2 ml of THF. After reaction at −20° C. for 2 hours, the reaction mixture was poured into a saturated solution of ammonium chloride. The resulting mixture was extracted with ethyl ether. The organic layer was washed with water and saturated saline and dried over magnesium sulfate. The solvent was then distilled off under reduced pressure. The residue was purified by chromatography on a silica gel column while using hexane-ethyl acetate, whereby 1,2-(ethylenedioxy)-3-(10-hydroxydecyl)-2-methyl-3-(phenylsulfonyl)-cyclohexane was obtained in the form of a colorless oil. Yield: 92%, TLC: (hexane-AcOEt: 6-4) Rf=0.2

(4) Paratoluenesulfonic acid (20 mg) was added to a solution of 388 mg of 1,1-(ethylenedioxy)-3-(10-hydroxydecyl)-2-methyl-3-(phenylsulfonyl)-cyclohexane in 30 ml of chloroform and 6 ml of acetone. The resulting mixture was reacted at 50° C. for 24 hours. To the reaction mixture was added 10 ml of a saturated aqueous solution of sodium bicarbonate, followed by extraction with sodium bicarbonate, followed by extraction with dichloromethane. The organic layer was washed with saturated saline and dried over magnesium sulfate. The solvent was distilled off under reduced pressure. The residue was purified by chromatography on a silica gel column while using hexane-ethyl acetate, whereby 3-(10-hydroxydecyl)-2-methyl-2-cyclohexen-1-one was obtained in the form of a colorless oil. Yield: 45%, TLC: (hexane-AcOEt: 6-4) Rf=0.2

In a similar manner to Preparation Example 16, the following compounds were obtained.

Preparation Example 17

3-(11-hydroxyundecyl)-2-methyl-2-cyclohexen-1-one (TLC: (hexane-AcOEt:6-4)Rf=0.24).

Preparation Example 18

3-(12-hydroxydodecyl)-2-methyl-2-cyclohexen-1-one (TLC: (hexane-AcOEt:6-4)Rf=0.26).

Preparation Example 19

3-(β-hydroxytridecyl)-2-methyl-2-cyclohexen-1-one (TLC: (hexane-AcOEt:6-4)Rf=0.28).

Preparation Example 20

3-(14-hydroxytetradecyl)-2-methyl-2-cyclohexen-1-one (TLC: (hexane-AcOEt:6-4)Rf=0.3).

Preparation Example 21

(1) To a solution of 1-phenylsulfonyl-2,6,6-trimethyl-1-cyclohexene (1 g, 3.5 mmol, 2 eq.) and triphenylmethane (4 mg) in dry THF (8 ml) was added n-butyllithium (1.4 M in hexane, 4 ml, 3 eq.) at −78° C. under argon. After stirring for 10 minutes, the mixture was stirred at room temperature and HMPA (1.5 ml) was added. After 1.5 hours at this temperature, the mixture was recooled at −78° C. and 11-bromo-undecanol (439 mg, 1.75 mmol, 1 eq.) was added slowly. The mixture was stirred for 3 hours at −20° C. and poured into a solution of saturated $NH_4Cl$ (40 ml). The solution was extracted with ether and the organic layer was washed with brine, dried with $MgSO_4$ and distilled off under reduce pressure. The residue was purified by chromatography over silica gel, eluting with hexane-AcOEt (8-2 to 6-4), to give 1-(12-hydroxydodecyl-1-phenylsulfonyl)-2,6,6-trimethyl-1-cyclohexene as a white solid (622 mg). TLC: (hexane-AcOEt: 6-4) Rf=0.43

(2) To a solution of 1-(12-hydroxydodecyl-1-phenylsulfonyl)-2,6,6-trimethyl-1-cyclohexene (579 mg, 1.29 mmol, 1 eq.) in dry ethanol (25 ml) was added $Na_2HPO_4$ (366 mg) and mercury-sodium amalgam (4 g) under argon. The mixture was stirred at room temperature for 1 hour, then quenched with 5% HCl, extracted with ether, washed with water, then dried with $MgSO_4$ and distilled off under reduced pressure to give 1-(12-acetoxydodecyl)-2,6,6-trimethyl-1-cyclohexene as a colorless oil (353 mg). TLC: (hexane-AcOEt: 5—5) Rf=0.75

(3) To a solution of 1-(12-acetoxydodecyl)-2,6,6-trimethyl-1-cyclohexene (321 mg) in cyclohexane (6 ml) was added water (0.8 ml), ruthenium trichloride hydrate (1.3 mg) and 70% t-BuOOH (1.26 ml). The solution was stirred at room temperature for 6 hours, filtered through a pad of celite and poured into a solution of 10% $Na_2SO_4$. The solution was extracted with ethanol, washed with brine, dried with $MgSO_4$ and distilled off under reduced pressure. The residue was purified by chromatography over silica gel to give 3-(12-acetoxydodecyl)-2,4,4-trimethyl-2-cyclohexen-1-one as a colorless oil (227 mg). TLC: (hexane-AcOEt: 3-7) Rf=0.68

(4) To a solution of 3-(12-acetoxydodecyl)-2,4,4-trimethyl-2-cyclohexene-1-one (132 mg) in dry methanol (8 ml) was added water (3 drops) and $K_2CO_3$ (74 mg). After stirring at room temperature for 2.5 hours the solution was neutralized at pH 7 with HCl 5%, extracted with ether, dried with $MgSO_4$ and distilled off under reduced pressure. The residue was purified by chromatography over silica gel to give 3-(12-hydroxydodecyl)-2,4,4-trimethyl-2-cyclohexene-1-one as a colorless oil (94 mg). TLC: (hexane-AcOEt: 7-3) Rf=0.2

In a similar manner to Preparation Example 21, the following compounds were obtained.

Preparation Example 22

3-(11-hydroxydodecyl)-2,4,4-trimethyl-2-cyclohexen-1-one (TLC: (hexane-AcOEt:7-3)Rf=0.2).

Preparation Example 23

3-(14-hydroxytetradecyl)-2,4,4-trimethyl-2-cyclohexen-1-one (TLC: (hexane-AcOEt:7-3)Rf=0.25).

Preparation Example 24

3-(15-hydroxypentadecyl)-2,4,4-trimethyl-2-cyclohexen-1-one (TLC: (hexane-AcOEt:7-3)Rf=0.29).

Preparation Example 25

3-(16-hydroxyhexadecyl)-2,4,4-trimethyl-2-cyclohexen-1-one (TLC: (hexane-AcOEt:7-3)Rf=0.26).

Test Example 1

Survival Test for Transgenic Mice Expressing an SOD-1 Mutant Gene

Ten transgenic mice were subjected to the survival test. The transgenic mice employed were those in which Gly-86 in the fourth exon of a mouse SOD-1 gene is mutated to Arg (G86R) (Ripps M. E., et al.: *Proc. Natl. Acad. Sci. USA.* 92: 689–693, 1995). The compound of Preparation Example 10 [3-(14-hydroxytetradecyl)-4-methyl-2-cyclohexen-1-one] was dissolved in ethanol/Tween 80/physiological saline (5/2.85/92.15). The solution was intraperitoneally (i.p.) administered to five specimens at an effective dose of 2 mg/kg for 40 continuous days, and physiological saline alone was similarly administered to the other five specimens. One mouse died due to injection complication before elapse of 90 days. The other four mice died at day 150. All control animals died at about day 90. The life was prolonged by 50% or more, which has high significance.

Excellent data have been obtained by dissolving the compound of Preparation Example 10 in water in the presence of dimethyl-beta-cyclodextrin (1/1 mole/mole).

All mice which were administered with the compound of Preparation Example 10 were very active during the test, whereas control mice were morbid and could not act appropriately.

Test Example 2

(1) Transgenic mice expressing an SOD-1 mutant gene were subjected to the survival test in the same manner as Test Example 1 except that 8 mg/kg of compound of Preparation Example 10 was intraperitoneally administered three times a week until the mice died. As a result, it was found that while the control mice were all died at around day 110, the mice to which were administered compound of Preparation Example 10 were died at around day 150 on average, two mice of them surviving more than 200 days. The life was prolonged by 30% or more.

(2) Meanwhile, during the survival test (1) of the transgenic mice, bar test for confirming the motor function was conducted. In this test, the mouse to which was administered compound of Preparation 10 and control mouse were compared in the time (seconds) required for their passing over a metallic bar having the size of 10 mm in diameter and 45 cm in length. The measurement was carried out from 80 days to 91 days after birth. As a consequence, as shown in FIG. 1, for both the mouse to which was administered compound of Preparation Example 10 and control mouse, the time for passing over the metallic bar became gradually shorter depending on the days passing from the initial date to the final date of the test. However, when compared the difference between the time at the initial date and the time at the final date, of the mouse to which was administered compound of Preparation Example 10 and of the control mouse, the ratio of the difference of the mouse to which was administered compound of Preparation Example 10 to the difference of the control mouse was about 40%. This result indicates that the mouse to which was administered compound of Preparation Example 10 was more active than the control mouse.

(3) Moreover, in the survival test of transgenic mice (1), onset day (i.e., the day from which mouse becomes impossible to move) was compared between the mouse to which was administered compound of Preparation Example 10 and the control mouse. As a result, for the mouse to which was administered compound of Preparation Example 10, when compared to the control mouse, a prolonged time to the onset day by 161 to 180 days was observed, onset day being prolonged by 20%.

Test Example 3

Neurite-Extension Effect

Neurons originating from the cerebral hemisphere of rat fetus (13–15 days) were used. The neurons were cultured according to a method described by Borg, J. et al. (Borg, J. et al.: *Dev. Brain Res.*, 18: 37, 1985). Neurons in an amount of $1.5 \times 10^5$ were dispersed on a polylysine-coated dish (35 mm), and DMEM (supplemented with insulin, transferrin, progesterone, sodium selenate, and putrescine) was added thereto in an amount of 3 ml. Compound (1) of the present invention was dissolved in ethanol, and then the solution was added thereto such that the concentration became $1 \times 10^{-8}$ M. The neurons had been cultured for three days without the culture medium being changed. Thereafter, the neurons were fixed by use of PBS containing 2% glutaraldehyde and observed under a phase-contrast microscope. The results are shown in Table 1.

TABLE 1

| Compound No. | Neurite-extension effect |
|---|---|
| 8 | +++ |
| 9 | ++++ |
| 10 | ++++ |
| 12 | ++ |
| 13 | +++ |
| 14 | +++ |
| 15 | +++ |
| 18 | ++ |
| 20 | ++++ |
| 22 | ++ |
| 23 | +++ |
| 24 | ++++ |
| BFGF | ++ |
| Negative control | 0 |

0: No effect,
+: Faintly effective,
++: Slightly effective,
+++: Effective >160%,
++++: Remarkably effective >200%

INDUSTRIAL APPLICABILITY

Since the compound (1) exhibits excellent neurite-extension ability and an inhibition effect on disorders caused by mutation in an SOD gene, it is useful as a preventive and therapeutic drug for neurodegenerative diseases, inter alia, amyotrophic lateral sclerosis, and as an inhibitory drug for disorders caused by mutation in an SOD gene.

The invention claimed is:

1. A method for treating amyotrophic lateral sclerosis, which comprises:
   administering to a subject in need thereof a cyclohexenone long-chain alcohol compound, pharmaceutically acceptable salt, solvate or hydrate thereof, represented by the following formula (1):

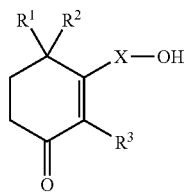

(1)

wherein each of $R^1$, $R^2$, and $R^3$ is a methyl group; and X is a C15–C28 linear alkylene group or a C15–C28 linear alkenylene group.

2. The method of claim 1, wherein X is a C15–C28 linear alkylene group.

3. The method of claim 1, wherein X is a C15–C28 linear alkenylene group.

4. The method of claim 1, wherein the administering is orally, by injection or by suppository.

5. The method of claim 1, wherein the daily dose for a human adult is 0.01–1000 mg.

6. The method of claim 1, wherein the daily dose for a human adult is 0.1–100 mg.

7. A method for treating amyotrophic lateral sclerosis caused by mutation in a superoxide dismutase gene, which comprises:

administering to a subject in need thereof a cyclohexenone long-chain alcohol compound, pharmaceutically acceptable salt, solvate or hydrate thereof, represented by the following formula (1):

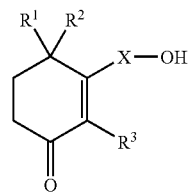

(1)

wherein each of $R^1$, $R^2$, and $R^3$ is a methyl group; and X is a C15–C28 linear alkylene group or a C15–C28 linear alkenylene group.

8. The method of claim 7, wherein the administering is orally, by injection or by suppository.

9. The method of claim 7, wherein the daily dose for a human adult is 0.01–1000 mg.

10. The method of claim 7, wherein the daily dose for a human adult is 0.1–100 mg.

* * * * *